United States Patent

Berthon-Jones

[11] Patent Number: 6,152,129
[45] Date of Patent: *Nov. 28, 2000

[54] DETERMINATION OF LEAK AND RESPIRATORY AIRFLOW

[75] Inventor: Michael Berthon-Jones, Leonay, Australia

[73] Assignee: ResMed Limited, North Ryde, Australia

[*] Notice: This patent issued on a continued prosecution application filed under 37 CFR 1.53(d), and is subject to the twenty year patent term provisions of 35 U.S.C. 154(a)(2).

[21] Appl. No.: 08/911,513

[22] Filed: Aug. 14, 1997

[30] Foreign Application Priority Data

Aug. 14, 1996 [AU] Australia .................................. PO1638

[51] Int. Cl.⁷ .................................................. A61M 15/00
[52] U.S. Cl. ............................... 128/200.24; 128/203.27; 128/203.26; 128/204.23
[58] Field of Search .......................... 128/200.24, 204.21, 128/204.23, 204.18, 203.12, 207.14

[56] References Cited

U.S. PATENT DOCUMENTS

| Re. 35,295 | 7/1996 | Estes et al. . |
| Re. 35,339 | 10/1996 | Rapoport . |
| 2,904,033 | 9/1959 | Shane . |
| 3,099,985 | 8/1963 | Wilson et al ....................... 128/203.11 |
| 3,559,638 | 2/1971 | Potter . |
| 3,595,228 | 7/1971 | Simon et al. . |
| 3,611,801 | 10/1971 | Paine et al. . |
| 3,741,208 | 6/1973 | Jonsson et al. .................... 128/204.21 |
| 3,783,893 | 1/1974 | Davison . |
| 3,802,417 | 4/1974 | Lang . |
| 3,817,246 | 6/1974 | Weigl . |
| 3,882,847 | 5/1975 | Jacobs . |
| 3,903,875 | 9/1975 | Hughes . |
| 3,914,994 | 10/1975 | Banner . |

(List continued on next page.)

FOREIGN PATENT DOCUMENTS

| A-62221/90 | 3/1991 | Australia . |
| A-76019/91 | 1/1992 | Australia . |
| A-33877/93 | 4/1993 | Australia . |
| B-59270/90 | 5/1993 | Australia . |

(List continued on next page.)

OTHER PUBLICATIONS

Derwent: Flowmeter for fluids—has turbine transducer and volumetric sensor for simultaneous calibration.
Mark Kantrowitz, Erik Horskotte and Cliff Joslyn; "Answers to Frequently Asked Questions About Fuzzy Logic and Fuzzy Expert Systems" Version 1.24 last Modified 20 2 96.
New! Breas PV 100 CPAP First Class Quality and Function. At the right Price; Jul. 4, 1998, pp. 1–2.
PV 101 Bi Level CPAP and PV 102 Bi–Level Time; pp. 1–3.
Prodigy Medical Supplies Co. Ltd.; CPAP.

(List continued on next page.)

Primary Examiner—John G. Weiss
Assistant Examiner—Teena Mitchell
Attorney, Agent, or Firm—Gottlieb, Rackman & Reisman, P.C.

[57] ABSTRACT

Methods and apparatus for determining leak and respiratory airflow are disclosed. A pressure sensor (34) and a differential pressure sensor (32) have connection with a pneumotach (24) to derive instantaneous mask pressure and airflow respectively. A microcontroller (38) estimates a non-linear conductance of any leak path occurring at a mask (12) as being the low pass filtered instantaneous airflow divided by the low pass filtered square root of the instantaneous pressure. The instantaneous leak flow is then the conductance multiplied by the square root of the instantaneous pressure, and the respiratory airflow is calculated as being the instantaneous airflow minus the instantaneous leak flow. The time constants for the low pass filtering performed by the microcontroller (38) can be dynamically adjusted dependent upon sudden changes in the instantaneous leak flow.

18 Claims, 10 Drawing Sheets

U.S. PATENT DOCUMENTS

| | | | |
|---|---|---|---|
| 3,932,054 | 1/1976 | McKelvey . | |
| 3,985,467 | 10/1976 | Lefferson . | |
| 3,989,037 | 11/1976 | Frabetzki . | |
| 3,992,598 | 11/1976 | Welsh et al. . | |
| 3,995,661 | 12/1976 | Van Fossen | 137/807 |
| 4,006,634 | 2/1977 | Billette et al. . | |
| 4,083,245 | 4/1978 | Osborn . | |
| 4,109,749 | 8/1978 | Sweet . | |
| 4,249,527 | 2/1981 | Ko et al. . | |
| 4,301,833 | 11/1981 | Donald, III . | |
| 4,312,235 | 1/1982 | Daigle . | |
| 4,320,766 | 3/1982 | Alihanka et al. . | |
| 4,322,594 | 3/1982 | Brisson . | |
| 4,381,788 | 5/1983 | Douglas . | |
| 4,387,722 | 6/1983 | Kearns . | |
| 4,396,034 | 8/1983 | Cherniak | 137/514 |
| 4,414,982 | 11/1983 | Durkan | 128/716 |
| 4,433,693 | 2/1984 | Hochstein . | |
| 4,448,058 | 5/1984 | Jaffe et al. . | |
| 4,449,525 | 5/1984 | White et al. | 128/203.11 |
| 4,499,914 | 2/1985 | Schebler . | |
| 4,506,666 | 3/1985 | Durkan . | |
| 4,530,334 | 7/1985 | Pagdin . | |
| 4,550,615 | 11/1985 | Grant . | |
| 4,550,726 | 11/1985 | McEwen . | |
| 4,558,710 | 12/1985 | Eichler | 128/720 |
| 4,570,631 | 2/1986 | Durkan . | |
| 4,576,179 | 3/1986 | Manus et al. . | |
| 4,579,114 | 4/1986 | Gray et al. | 128/203.11 |
| 4,580,575 | 4/1986 | Birnbaum et al. . | |
| 4,595,016 | 6/1986 | Fertig et al. . | |
| 4,602,644 | 7/1986 | DiBenedetto et al. . | |
| 4,630,614 | 12/1986 | Atlas . | |
| 4,648,396 | 3/1987 | Raemer . | |
| 4,648,407 | 3/1987 | Sackner . | |
| 4,655,213 | 4/1987 | Rapoport et al. . | |
| 4,677,975 | 7/1987 | Edgar et al. | 128/200.14 |
| 4,686,974 | 8/1987 | Sato et al. . | |
| 4,686,999 | 8/1987 | Synder et al. . | |
| 4,738,266 | 4/1988 | Thatcher . | |
| 4,773,411 | 9/1988 | Downs | 128/204.18 |
| 4,777,963 | 10/1988 | McKenna . | |
| 4,795,314 | 1/1989 | Prybella et al. . | |
| 4,802,485 | 2/1989 | Bowers et al. . | |
| 4,803,471 | 2/1989 | Rowland . | |
| 4,819,629 | 4/1989 | Jonson | 128/203.22 |
| 4,823,788 | 4/1989 | Smith et al. . | |
| 4,825,802 | 5/1989 | Le Bec . | |
| 4,827,922 | 5/1989 | Champain et al. . | |
| 4,838,258 | 6/1989 | Dryden et al. . | |
| 4,844,085 | 7/1989 | Gattinoni . | |
| 4,856,506 | 8/1989 | Jinotti | 128/203.11 |
| 4,860,766 | 8/1989 | Sackner . | |
| 4,870,960 | 10/1989 | Hradek . | |
| 4,870,963 | 10/1989 | Carter . | |
| 4,913,401 | 4/1990 | Handke . | |
| 4,915,103 | 4/1990 | Visveshwara et al. . | |
| 4,938,210 | 7/1990 | Shene | 128/203.12 |
| 4,938,212 | 7/1990 | Snook et al. . | |
| 4,944,310 | 7/1990 | Sullivan . | |
| 4,957,107 | 9/1990 | Sipin . | |
| 4,960,118 | 10/1990 | Pennock . | |
| 4,971,065 | 11/1990 | Pearce . | |
| 4,972,842 | 11/1990 | Korten et al. . | |
| 4,982,738 | 1/1991 | Griebel . | |
| 4,986,269 | 1/1991 | Hakkinen | 128/204.23 |
| 4,989,599 | 2/1991 | Carter . | |
| 5,009,635 | 4/1991 | Scarberry . | |
| 5,024,219 | 6/1991 | Dietz . | |
| 5,052,400 | 10/1991 | Dietz . | |
| 5,063,922 | 11/1991 | Hakkinen | 128/200.16 |
| 5,065,756 | 11/1991 | Rapoport . | |
| 5,069,222 | 12/1991 | McDonald, Jr. . | |
| 5,090,248 | 2/1992 | Cimmino et al. . | |
| 5,105,354 | 4/1992 | Nishimura . | |
| 5,117,819 | 6/1992 | Servidio et al. . | |
| 5,134,995 | 8/1992 | Gruenke et al. . | |
| 5,148,802 | 9/1992 | Sanders et al. . | |
| 5,161,525 | 11/1992 | Kimm et al. . | |
| 5,161,541 | 11/1992 | Bowman et al. . | |
| 5,170,798 | 12/1992 | Riker . | |
| 5,174,287 | 12/1992 | Kallok et al. | 128/419 |
| 5,178,138 | 1/1993 | Walstrom et al. | 128/200.23 |
| 5,183,983 | 2/1993 | Knop . | |
| 5,190,048 | 3/1993 | Wilkinson . | |
| 5,195,528 | 3/1993 | Hok . | |
| 5,199,424 | 4/1993 | Sullivan et al. . | |
| 5,203,343 | 4/1993 | Axe et al. . | |
| 5,230,330 | 7/1993 | Price | 128/203.11 |
| 5,231,979 | 8/1993 | Rose et al. . | |
| 5,231,983 | 8/1993 | Matson et al. | 128/207.14 |
| 5,233,983 | 8/1993 | Markowitz . | |
| 5,239,995 | 8/1993 | Estes et al. . | |
| 5,245,995 | 9/1993 | Sullivan et al. . | |
| 5,259,373 | 11/1993 | Gruenke et al. . | |
| 5,271,391 | 12/1993 | Graves . | |
| 5,280,784 | 1/1994 | Kohler | 128/200.14 |
| 5,293,864 | 3/1994 | McFadden . | |
| 5,295,491 | 3/1994 | Gevins . | |
| 5,303,700 | 4/1994 | Weismann et al. . | |
| 5,305,787 | 4/1994 | Thygesen . | |
| 5,311,875 | 5/1994 | Stasz . | |
| 5,313,937 | 5/1994 | Zdrojkowski . | |
| 5,322,057 | 6/1994 | Raabe et al. | 128/203.12 |
| 5,327,899 | 7/1994 | Harris et al. . | |
| 5,335,654 | 8/1994 | Rapoport . | |
| 5,343,878 | 9/1994 | Scarberry et al. . | |
| 5,343,898 | 9/1994 | Scarberry et al. . | |
| 5,353,788 | 10/1994 | Miles . | |
| 5,360,008 | 11/1994 | Campbell, Jr. . | |
| 5,388,571 | 2/1995 | Roberts et al. | 128/203.12 |
| 5,394,882 | 3/1995 | Mawhinney . | |
| 5,398,673 | 3/1995 | Lambert | 128/202.28 |
| 5,404,871 | 4/1995 | Goodman et al. | 128/200.14 |
| 5,413,111 | 5/1995 | Wilkinson . | |
| 5,433,193 | 7/1995 | Sanders et al. . | |
| 5,438,980 | 8/1995 | Phillips . | |
| 5,443,061 | 8/1995 | Champain et al. . | |
| 5,443,075 | 8/1995 | Holscher . | |
| 5,448,996 | 9/1995 | Bellin et al. . | |
| 5,458,137 | 10/1995 | Axe et al. . | |
| 5,479,920 | 1/1996 | Piper et al. | 128/204.23 |
| 5,479,939 | 1/1996 | Ogino . | |
| 5,483,969 | 1/1996 | Testerman et al. . | |
| 5,490,502 | 2/1996 | Rapoport et al. . | |
| 5,492,113 | 2/1996 | Estes et al. . | |
| 5,503,146 | 4/1996 | Froehlich et al. . | |
| 5,507,282 | 4/1996 | Younes . | |
| 5,509,404 | 4/1996 | Lloyd et al. | 128/200.14 |
| 5,513,631 | 5/1996 | McWilliams . | |
| 5,517,983 | 5/1996 | Deighan et al. . | |
| 5,522,382 | 6/1996 | Sullivan et al. . | |
| 5,526,805 | 6/1996 | Lutz et al. . | |
| 5,535,738 | 7/1996 | Estes et al. . | |
| 5,535,739 | 7/1996 | Rapoport et al. . | |
| 5,537,997 | 7/1996 | Mechlenburg et al. . | |
| 5,540,219 | 7/1996 | Mechlenburg et al. . | |
| 5,540,220 | 7/1996 | Gropper . | |
| 5,540,733 | 7/1996 | Testerman et al. . | |
| 5,546,933 | 8/1996 | Rapoport et al. . | |
| 5,546,952 | 8/1996 | Erickson . | |
| 5,549,106 | 8/1996 | Gruenke et al. . | |

| | | |
|---|---|---|
| 5,549,655 | 8/1996 | Erickson . |
| 5,551,418 | 9/1996 | Estes et al. . |
| 5,551,419 | 9/1996 | Froehlich et al. . |
| 5,558,099 | 9/1996 | Bowman et al. . |
| 5,567,127 | 10/1996 | Wentz . |
| 5,570,682 | 11/1996 | Johnson . |
| 5,588,439 | 12/1996 | Hollub . |
| 5,598,838 | 2/1997 | Servidio et al. . |
| 5,605,151 | 2/1997 | Lynn . |
| 5,608,647 | 3/1997 | Rubsamen et al. ............ 364/509 |
| 5,617,846 | 4/1997 | Graetz et al. . |
| 5,630,411 | 5/1997 | Holscher . |
| 5,632,269 | 5/1997 | Zedrojkowski . |
| 5,642,730 | 7/1997 | Baran ............... 128/207.14 |
| 5,645,053 | 7/1997 | Remmers et al. . |
| 5,645,054 | 7/1997 | Cotner et al. . |
| 5,647,351 | 7/1997 | Weismann et al. . |
| 5,655,520 | 8/1997 | Howe et al. ............ 128/203.12 |
| 5,655,522 | 8/1997 | Mechlenburg et al. . |
| 5,660,171 | 8/1997 | Kimm et al. . |
| 5,666,946 | 9/1997 | Langenback . |
| 5,682,878 | 11/1997 | Ogden . |
| 5,685,296 | 11/1997 | Zdorjkowski et al. . |
| 5,701,883 | 12/1997 | Hete et al. . |
| 5,704,345 | 1/1998 | Berthon-Jones . |
| 5,715,812 | 2/1998 | Deighan et al. . |
| 5,730,119 | 3/1998 | Lekholm ............... 128/200.24 |
| 5,730,121 | 3/1998 | Hawkins et al. . |
| 5,740,795 | 4/1998 | Brydon . |
| 5,740,796 | 4/1998 | Skog ............... 128/204.23 |
| 5,743,253 | 4/1998 | Castor et al. ............ 128/200.24 |
| 5,794,615 | 8/1998 | Estes . |
| 5,797,852 | 8/1998 | Karakasoglu et al. . |
| 5,803,066 | 9/1998 | Rapoport et al. ............ 128/204.23 |
| 5,823,187 | 10/1998 | Estes et al. . |
| 5,845,636 | 12/1998 | Gruenke et al. ............ 128/204.23 |

FOREIGN PATENT DOCUMENTS

| | | |
|---|---|---|
| A-38508/93 | 7/1993 | Australia . |
| A-48748/93 | 9/1993 | Australia . |
| A-52628/93 | 12/1993 | Australia . |
| A-52628/93 | 7/1994 | Australia . |
| A-39130/95 | 12/1994 | Australia . |
| B 79174/94 | 6/1995 | Australia . |
| A-34471/95 | 2/1996 | Australia . |
| A-40711-95 | 4/1996 | Australia . |
| A-40711/95 | 4/1996 | Australia . |
| B 34354/95 | 5/1996 | Australia . |
| A 39130/95 | 6/1996 | Australia . |
| 0388 525 A1 | 9/1960 | European Pat. Off. . |
| 0 066 451 A1 | 12/1982 | European Pat. Off. . |
| B1 0 088 761 | 9/1983 | European Pat. Off. . |
| 0 164 500 A2 | 3/1985 | European Pat. Off. . |
| 0 171 321 A1 | 2/1986 | European Pat. Off. . |
| 0 185 980 A2 | 7/1986 | European Pat. Off. . |
| 0 236 850 A2 | 9/1987 | European Pat. Off. . |
| 298 367 A2 | 1/1989 | European Pat. Off. . |
| 0 425 092 A1 | 9/1989 | European Pat. Off. . |
| 0 452 001 A2 | 3/1990 | European Pat. Off. . |
| 0 425 092 A1 | 5/1991 | European Pat. Off. . |
| 0 461 281 A1 | 12/1991 | European Pat. Off. . |
| 481 459 A1 | 4/1992 | European Pat. Off. . |
| 0 062 166 A2 | 10/1992 | European Pat. Off. . |
| 0514 744 | 11/1992 | European Pat. Off. . |
| 0549299 A2 | 6/1993 | European Pat. Off. . |
| 606 687 A2 | 7/1994 | European Pat. Off. . |
| 0705615 A1 | 9/1994 | European Pat. Off. . |
| 0 714 670 A2 | 12/1994 | European Pat. Off. . |
| 0651971 A1 | 5/1995 | European Pat. Off. . |
| 0 656 216 A2 | 6/1995 | European Pat. Off. . |
| 0 661 071 A1 | 7/1995 | European Pat. Off. . |
| 178 925 A2 | 4/1996 | European Pat. Off. . |
| 0 709 107 A1 | 5/1996 | European Pat. Off. . |
| 0 714 670 A2 | 6/1996 | European Pat. Off. . |
| 0 765 631 A2 | 4/1997 | European Pat. Off. . |
| 0 788 805 A2 | 8/1997 | European Pat. Off. . |
| 0 839 545 A1 | 5/1998 | European Pat. Off. . |
| 0 872 643 A2 | 10/1998 | European Pat. Off. . |
| 2 574 657 A1 | 6/1986 | France . |
| 2 672 221 | 8/1992 | France . |
| 2682042 A1 | 4/1993 | France . |
| 459104 | 4/1928 | Germany . |
| 3015279 A1 | 10/1981 | Germany . |
| 34 02 603 A1 | 1/1984 | Germany . |
| 3345067 A1 | 6/1984 | Germany . |
| 3429345 A1 | 6/1985 | Germany . |
| 3537507 A1 | 4/1987 | Germany . |
| 3539073 A1 | 5/1987 | Germany . |
| 4432219 C1 | 4/1996 | Germany . |
| 296 12 199 U1 | 12/1996 | Germany . |
| 195 36 632 A1 | 3/1997 | Germany . |
| 06249739 | 9/1994 | Japan . |
| 06249740 | 9/1994 | Japan . |
| 06249741 | 9/1994 | Japan . |
| 6-249742 | 9/1994 | Japan . |
| 6-249743 | 9/1994 | Japan . |
| 6-249744 | 9/1994 | Japan . |
| 8019610 | 1/1996 | Japan . |
| 467041 | 5/1992 | Sweden . |
| 1710064 A1 | 2/1994 | Sweden . |
| 1 444 053 | 7/1976 | United Kingdom . |
| 1583273 | 1/1981 | United Kingdom . |
| 2 077 444 | 12/1981 | United Kingdom . |
| 2 147 506 | 5/1985 | United Kingdom . |
| 2 164 569 | 3/1986 | United Kingdom . |
| 2 166 871 | 5/1986 | United Kingdom . |
| 2 205 167 | 11/1988 | United Kingdom . |
| 2 221 302 | 1/1990 | United Kingdom . |
| 2 254 700 | 10/1992 | United Kingdom . |
| 2 261 290 | 5/1993 | United Kingdom . |
| 2 271 811 | 4/1994 | United Kingdom . |
| 2 294 400 | 5/1996 | United Kingdom . |
| 1432572 | 4/1997 | United Kingdom . |
| WO 80/01044 | 5/1980 | WIPO . |
| WO 82/03326 | 10/1982 | WIPO . |
| WO 82/03548 | 10/1982 | WIPO . |
| WO 86/05965 | 10/1986 | WIPO . |
| WO 86/06969 | 12/1986 | WIPO . |
| WO 87/02577 | 5/1987 | WIPO . |
| WO 89/09565 | 10/1988 | WIPO . |
| WO 88/10108 | 12/1988 | WIPO . |
| WO 90/09146 | 8/1990 | WIPO . |
| WO 90/14121 | 11/1990 | WIPO . |
| WO 91/12051 | 8/1991 | WIPO . |
| WO 91/19456 | 12/1991 | WIPO . |
| WO 92/11054 | 7/1992 | WIPO . |
| WO 92/15353 | 9/1992 | WIPO . |
| WO 92/22244 | 12/1992 | WIPO . |
| WO 93/08857 | 5/1993 | WIPO . |
| WO 93/09834 | 5/1993 | WIPO . |
| WO 93/21982 | 11/1993 | WIPO . |
| WO 93/24169 | 12/1993 | WIPO . |
| WO 94/04071 | 3/1994 | WIPO . |
| WO 94/16759 | 8/1994 | WIPO . |
| WO 94/20018 | 9/1994 | WIPO . |
| WO 94/20051 | 9/1994 | WIPO . |
| WO 94/23780 | 10/1994 | WIPO . |
| WO 95/32016 | 11/1995 | WIPO . |
| WO 95/34917 | 12/1995 | WIPO . |
| WO 96/16688 | 6/1996 | WIPO . |
| WO 96/32055 | 10/1996 | WIPO . |
| WO 96/36279 | 11/1996 | WIPO . |

| | | |
|---|---|---|
| WO 96/40337 | 12/1996 | WIPO . |
| WO 96/41571 | 12/1996 | WIPO . |
| WO 97/02064 | 1/1997 | WIPO . |
| WO 97/05824 | 2/1997 | WIPO . |
| WO 97/10019 | 3/1997 | WIPO . |
| WO 97/10868 | 3/1997 | WIPO . |
| WO 97/14354 | 4/1997 | WIPO . |
| WO 97/15343 | 5/1997 | WIPO . |
| WO 97/18752 | 5/1997 | WIPO . |
| WO 97/20499 | 6/1997 | WIPO . |
| WO 97/22377 | 6/1997 | WIPO . |
| WO 97/28838 | 8/1997 | WIPO . |
| WO 97/41812 | 11/1997 | WIPO . |
| WO 98/06449 | 2/1998 | WIPO . |
| WO 98/25662 | 6/1998 | WIPO . |
| WO 98/33433 | 8/1998 | WIPO . |
| WO 98/35715 | 8/1998 | WIPO . |
| WO 98/36245 | 8/1998 | WIPO . |
| WO 98/36338 | 8/1998 | WIPO . |
| WO 98/47554 | 10/1998 | WIPO . |
| WO 98/52467 | 11/1998 | WIPO . |
| WO 98/57691 | 12/1998 | WIPO . |

OTHER PUBLICATIONS

Puritan Bennett; Companion 318 Nasal CPAP System; May 1993.
Nellcor Puritan Bennett; Announcing the Goodnight 314 and GoodKnight 318 Nasal CPAP Systems.
Puritan Bennett; Clean, Quiet, and Comfortable . . . The Companion's 515 Nasal CPAP System; Jun. 1988.
DeVilbiss Night Guard Nasal CPAP for the Treatment of Obstructive Sleep Apnea.
Devilbiss; Revitalizer Soft Start; The Facts Speak for Themselves.
Tranquility; Performance CPAP Advantage.
Healthdyne International; Tranquility Plus.
Respironics Inc.; Respironics' Solo CPAP System Provides Simplified OSA Therapy at an Outstanding value; Sep. 19, 1996.
Respironics Inc.: The First Family of OSA Therapy; 1991.
Fisher & Paykel Healthcare; HC200 Series Nasal CPAP Blower & Heated Humidifier.
Pierre Medical; Morphee Plus appareil de traitement des apnees du sommeil manuel d'utilisation.
Weinmann:Hamburg; Somnotron nCPAP–Great WM 2300.
Puritan Bennett; 515a Part of Our Blueprint for the Future; Mar. 1990.
Puritan Bennett; Companion 320 I/E Bi–Level Respiratory System; Apr. 1993.
ResMed; Sullivan VPAP II & II ST.
ResMed; The Sullivan V Family of CPAP Systems.
ResMed; The AutoSet Portable II.
ResMed; Sullivan Nasal CPAP System.
ResMed; The Sullivan IIID.
ResMed; The Sullivan Comfort.
DeVilbiss a Division of Sunrise Medical; Expand your Horizons With The Horizons.
Healthdyne Technologies; Home Health Care Dealer; The Journal of Home Medical Equipment and Services/Supplier; Nov. and Dec. 1997.
Healthdyne International; Transquility Quest, The Compact CPAP for Greater patient comfort.
AirStep; Medical Products . . . Stand the Test of Time.
MAP Medical Progress for Physician und Patient; The Gentle Therapy for Sleep–Related Breathing Disorders.
Taema; Ventilation CP 90.
DPAP; Breath, by breath, by breath.
Lifecare; Smallest. Quietest. Smartest.
Lifecare; Quiet CPAP System for Maximum Compliance; 1991.
Lifecare; Software Nasal Mask, Custom Nasal Masks; 1991.
Nidek Medical; Silenzio.
Weinmann; Just to Fell Well, Sensitive Sleep Apnoea Therapy with Somnotron 3 and Somno–Mask System
Respironics Inc.; Aria CPAP System.
Respironics Inc.; SleepEasy III A New Dawn in Patient Compliance.
Respironics Inc.; Muliple Choice REMstar Choice Nasal CPAP System.
MaxII nCPAP and Moritz II Bi–Level Brochure.

MEASURED MASK FLOW (L/sec)

CALCULATED LEAK (L/sec)

CALCULATED RESP. AIRFLOW (L/sec)

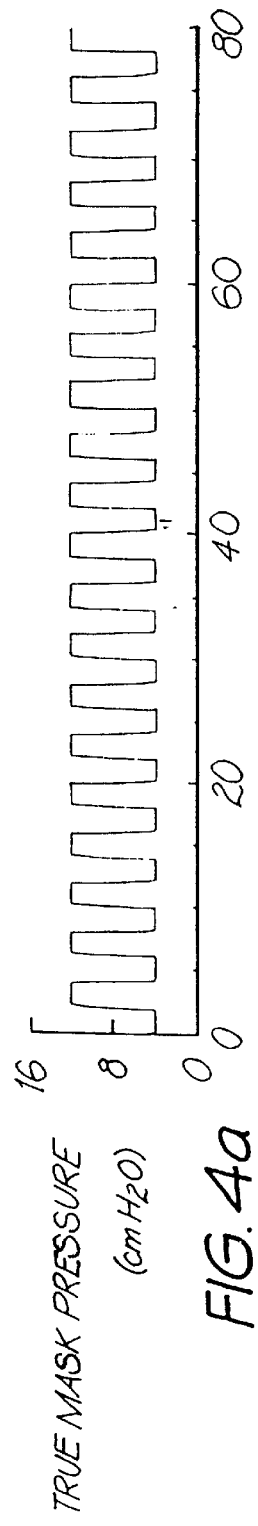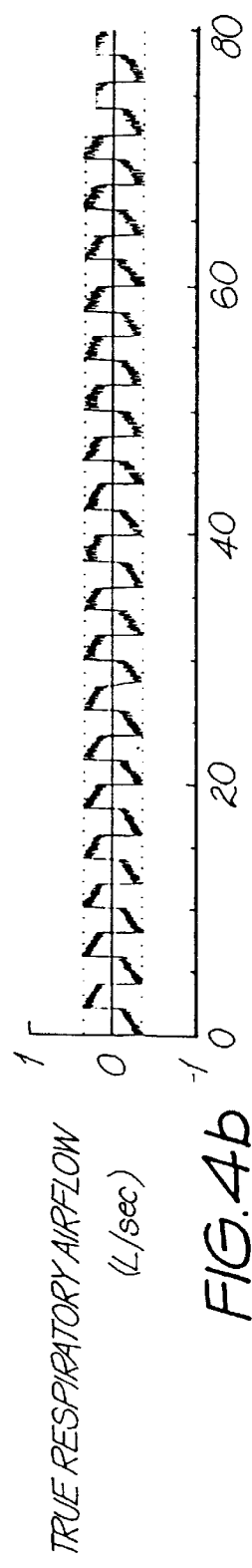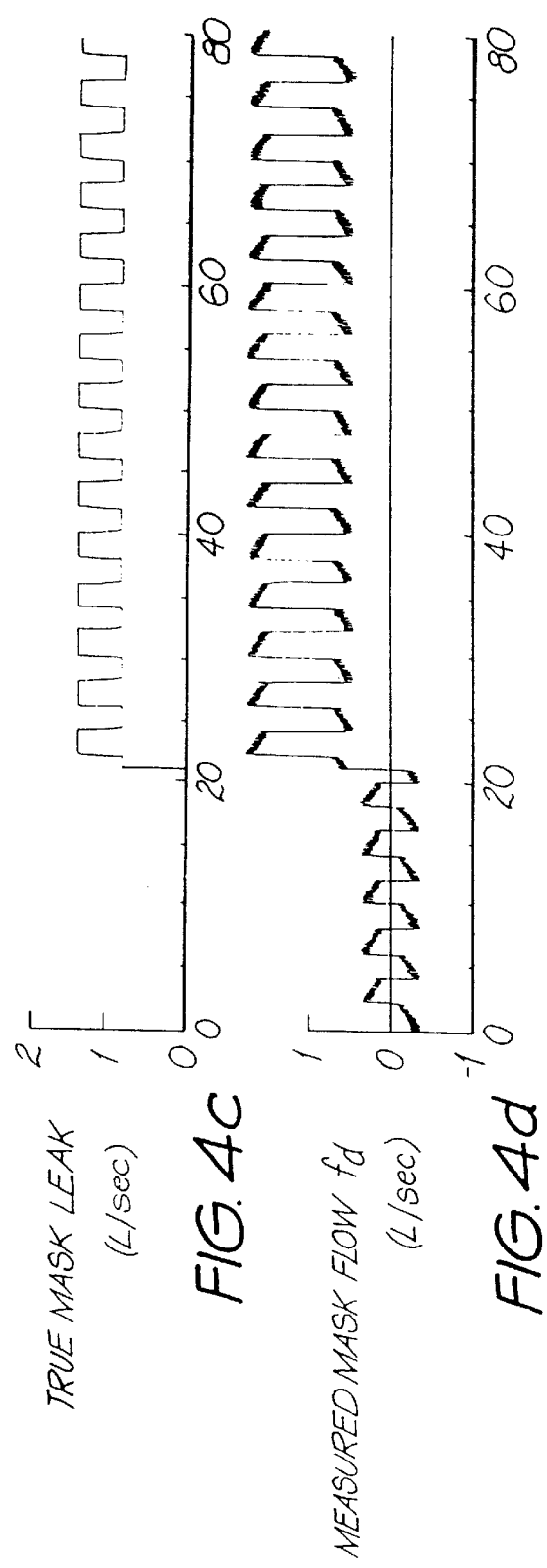
FIG. 4a TRUE MASK PRESSURE (cm H2O)
FIG. 4b TRUE RESPIRATORY AIRFLOW (L/sec)
FIG. 4c TRUE MASK LEAK (L/sec)
FIG. 4d MEASURED MASK FLOW $f_d$ (L/sec)

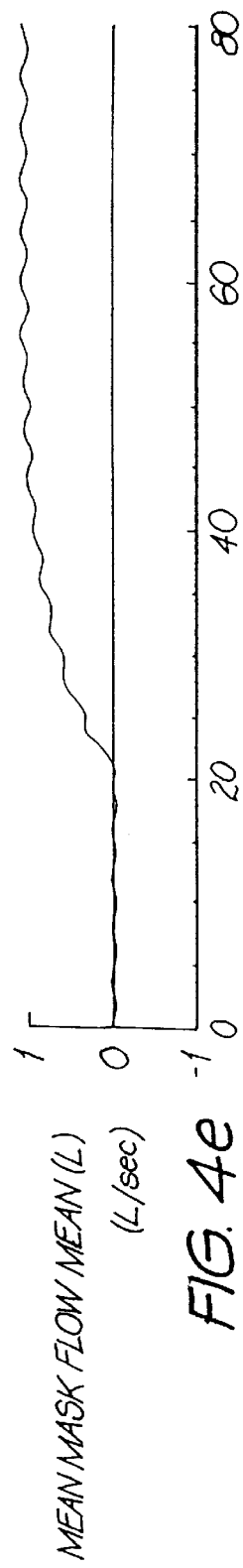
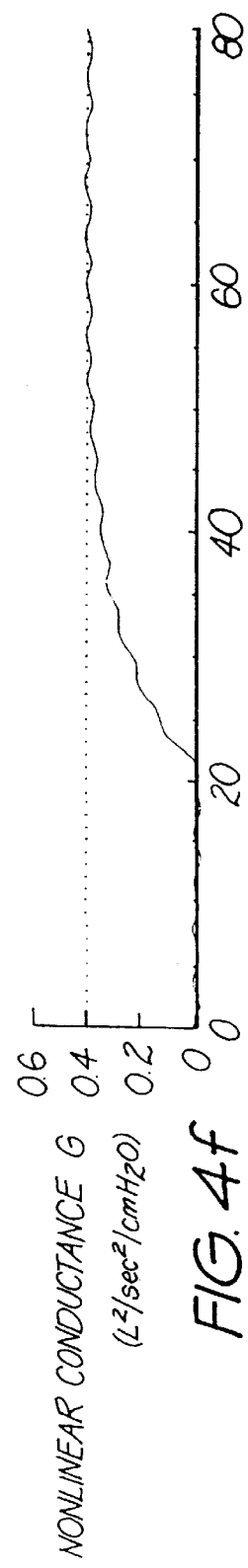
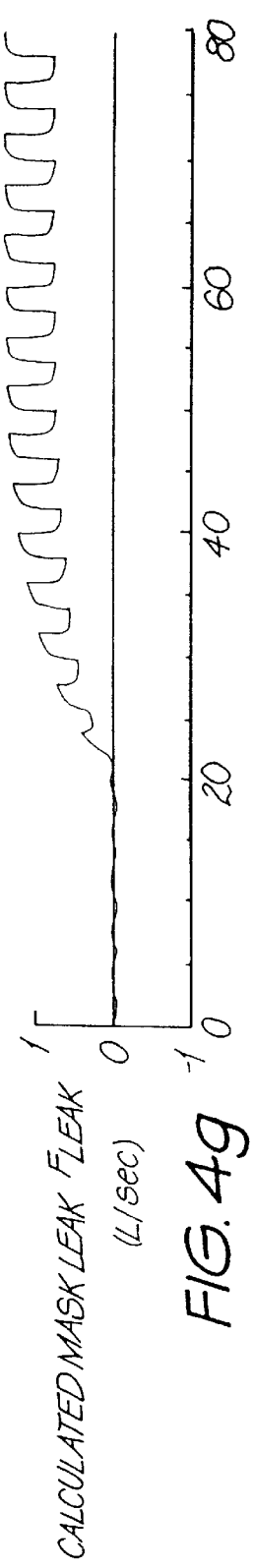
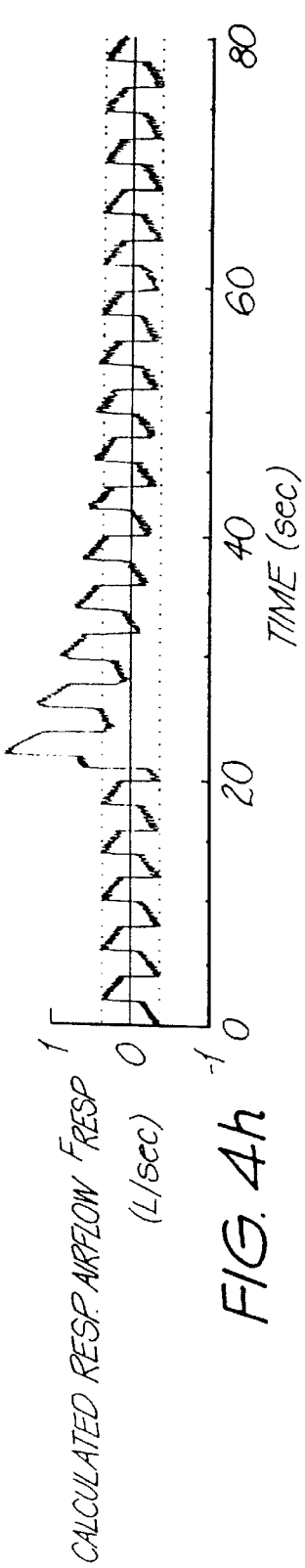

DETERMINATION OF LEAK AND RESPIRATORY AIRFLOW

FIELD OF THE INVENTION

The invention relates to methods and apparatus for the determination of leakage airflow and true respiratory airflow, particularly during mechanical ventilation.

The airflow determination can be for a subject who is either spontaneously or non-spontaneously breathing, or moves between these breathing states. The invention is especially suitable for, but not limited to, normally conscious and spontaneously breathing human subjects requiring long term ventilatory assistance, particularly during sleep.

BACKGROUND OF THE INVENTION

In this specification any reference to a "mask" is to be understood as including all forms of devices for passing breathable gas to a person's airway, including nose masks, nose and mouth masks, nasal prongs/pillows and endotracheal or tracheostomy tubes.

During mechanical ventilation, breathable gas is supplied for example via a mask, at a pressure which is higher during inspiration and lower during expiration. It is useful to measure the subject's respiratory airflow during mechanical ventilation to assess adequacy of treatment, or to control the operation of the ventilator.

Respiratory airflow is commonly measured with a pneumotachograph placed in the gas delivery path between the mask and the ventilator. Leaks between the mask and the subject are unavoidable. The pneumotachograph measures the sum of the respiratory airflow plus the flow through the leak. If the instantaneous flow through the leak is known, the respiratory airflow can he calculated by subtracting the flow through the leak from the flow at the pneumotach.

Known methods to correct for the flow through the leak assume (i) that the leak is substantially constant, and (ii) that over a sufficiently long time, inspiratory and expiratory respiratory airflow will cancel. If these assumptions are met, the average flow through the pneumotach over a sufficiently long period will equal the magnitude of the leak, and the true respiratory airflow may then be calculated as described.

The known method is only correct if the pressure at the mask is constant. If the mask pressure varies with time (for example, in the case of a ventilator), assumption (i) above will be invalid, and the calculated respiratory airflow will therefore be incorrect. This is shown markedly in FIGS. 1a–1f.

FIG. 1a shows a trace of measured mask pressure in bi-level CPAP treatment between about 4 cm H$_2$O on expiration and 12 cm H$_2$O on inspiration. FIG. 1b shows a trace of true respiratory airflow in synchronism with the mask pressures. At time=21 seconds a mask leak occurs, resulting in a leakage flow from the leak that is a function of the treatment pressure, as shown in FIG. 1c. The measured mask flow shown in FIG. 1d now includes an ofifset due to the leak flow. The prior art method then determines the calculated leak flow over a number of breaths, as shown in FIG. 1e. The resulting calculated respiratory flow, as the measured flow minus the calculating leak flow is shown in FIG. 1f, having returned to the correct mean value, however is incorrectly scaled in magnitude, giving a false indication of peak positive and negative airflow.

Another prior art arrangement is disclosed in European Publication No. 0 714 670 A2, including a calculation of a pressure-dependent leak component. The methodology relies on knowing precisely the occurrence of the start of an inspiratory event and the start of the next inspiratory event. In other words, the leak calculation is formed as an average over a known breath and applied to a subsequent breath.

This method cannot be used if the moment of start and end of the previous breath are unknown. In general, it can be difficult to accurately calculate the time of start of a breath. This is particularly the case immediately following a sudden change in the leak.

Furthermore, the method will not work in the case of a subject who is making no respiratory efforts, and is momentarily not being ventilated at all, for example during an apnea, because for the duration of the apnea there is no start or end of breath over which to make a calculation.

The present invention seeks to provide a determination of leak flow and true respiratory airflow, accounting for the variations in flow through a leak as a function of pressure.

SUMMARY OF THE INVENTION

The invention discloses a method for determining instantaneous leak flow at a mask having a leak path during mechanical ventilation, the method comprising the steps of:
 (a) determining instantaneous airflow at the mask;
 (b) determining instantaneous pressure at the mask;
 (c) estimating non-linear conductance of said leak path as the low-pass filtered instantaneous airflow divided by the low-pass filtered square root of the instantaneous pressure; and
 (d) determining said instantaneous leak flow to be said conductance multiplied by the square root of the said instantaneous pressure.

The invention further discloses a method for determining instantaneous respiratory airflow for a subject receiving breathable gas by a mask and in the presence of any mask leak, the method comprising the steps of:
 (a) determining instantaneous airflow at the mask;
 (b) determining instantaneous pressure at the mask;
 (c) estimating non-linear conductance of said leak path as the low pass filtered instantaneous airflow divided by the low pass filtered square root of the instantaneous pressure;
 (d) determining instantaneous leak flow to be said conductance multiplied by the square root of the said instantaneous pressure; and
 (e) calculating the respiratory airflow as the instantaneous airflow minus the instantaneous leak flow.

The invention yet further discloses apparatus for determining respiratory airflow for a subject receiving breathable gas by a mask and in the presence of any mask leak, the apparatus comprising:
 transducer means located at or proximate the mask to determine instantaneous mask airflow and pressure; and
 processing means for estimating non-linear conductance of said leak path as the low pass filtered instantaneous airflow divided by the low pass filtered square root of the instantaneous pressure, determining instantaneous leak flow to be said conductance multiplied by the square root of the said instantaneous pressure, and calculating the respiratory airflow as the instantaneous airflow minus the instantaneous leak flow.

The invention yet further discloses apparatus for providing continuous positive airway pressure treatment or mechanical ventilation, the apparatus comprising:

a turbine for the generation of a supply of breathable gas;

a gas delivery tube having connection with the turbine;

a mask having connection to the delivery tube to supply said breathable gas to a subject's airway;

transducer means located at or proximate the mask to determine instantaneous mask airflow and pressure;

processor means for estimating non-linear conductance of said leak path as the low pass filtered instantaneous airflow divided by the low pass filtered square root of the instantaneous pressure, determining instantaneous leak flow to be said conductance multiplied by the square root of the said instantaneous pressure, and calculating the respiratory airflow as the instantaneous airflow minus the instantaneous leak flow; and control means to control the flow generator to, in turn, control the mask pressure and/or mask airflow on the basis of the calculated respiratory airflow.

The invention yet further discloses a computer program for executing the steps referred to above.

In one preferred form, time constants of the low pass filtering are dynamically adjusted dependent upon sudden changes in the instantaneous leak flow.

Embodiments of the invention provide advantages over the prior art. There is no need to know when transitions between respiratory phases occurs. The independence from knowledge of the subject's respiratory state has the important result that the leak flow calculation is accurate in apneic (i.e. no flow) instances on the part of the subject or the mechanical ventilator.

BRIEF DESCRIPTION OF THE DRAWINGS

Embodiments of the invention will now be described with reference to the accompanying drawings in which:

FIG. 4 shows traces of pressure, airflow and other variables from which respiratory airflow is calculated;

DETAILED DESCRIPTION OF THE PREFERRED EMBODIMENTS

Figure 2A:
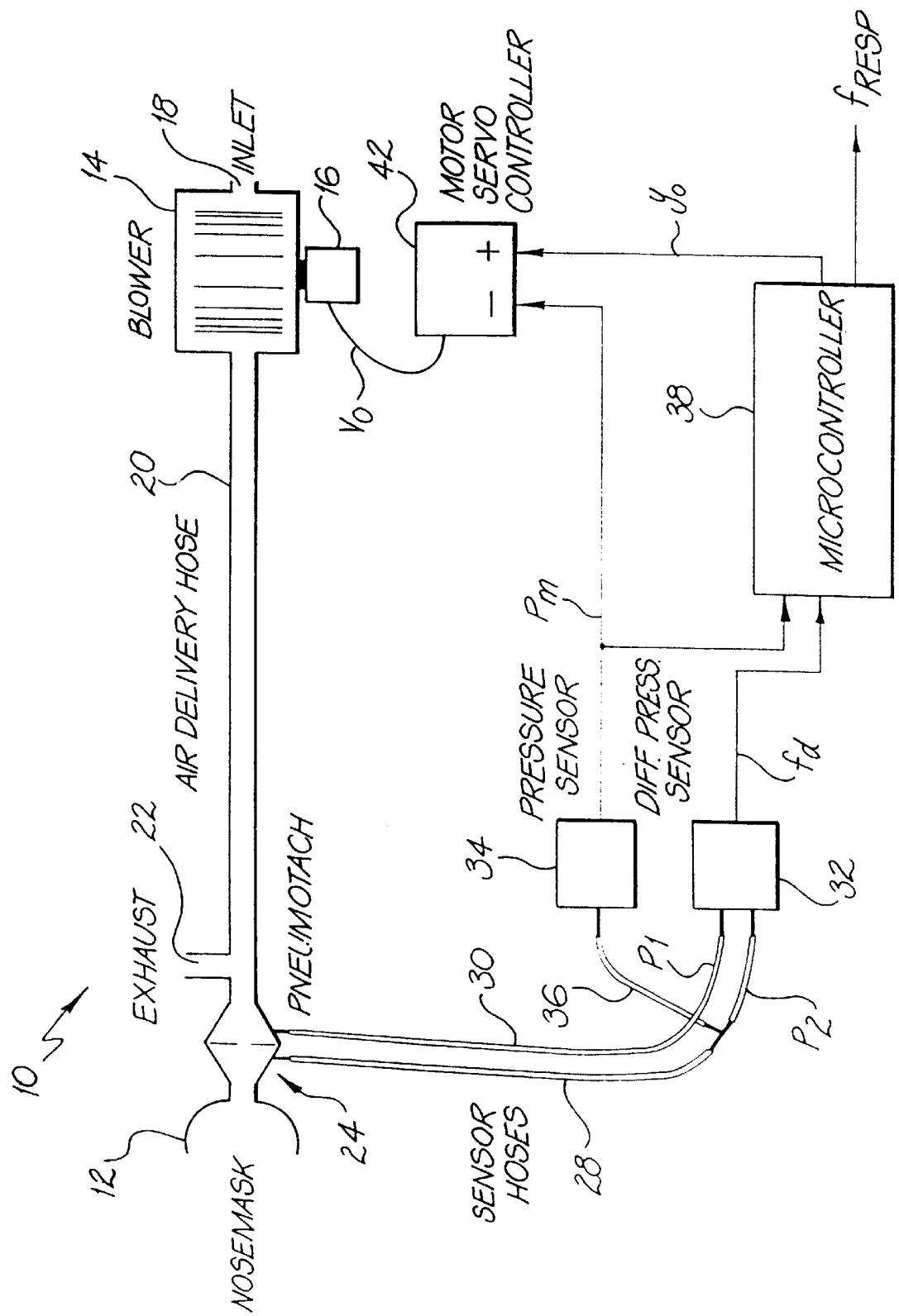
FIGS. 2a and b show schematic diagrams of two embodiments of ventilatory assistance apparatus.

FIG. 2a shows mechanical ventilation apparatus 10 embodying the invention.

The subject/patient wears a nose mask 12 of any known type. The subject equally could wear a face mask or nasal prongs/pillows, or alternatively have an endotracheal tube or tracheostomy tube in place. A turbine/blower 14, operated by a mechanically coupled electrical motor 16, receives air or breathable gas at an inlet 18 thereof, and supplies the breathable gas at a delivery pressure to a delivery tube/hose 20 having connection at the other end thereof with the nose mask 12. Breathable gas thus is provided to the subject's airway for the purpose of providing assisted respiration, with the subject's expired breath passing to atmosphere by an exhaust 22 in the delivery tube 20, typically located proximate to the mask 12.

A pneumotachograph 24 is placed in the delivery tube 20 between the mask 12 and the exhaust 22 to provide two pressure signals, $P_2$ and $P_1$, across the pneumotachograph, each passed by hoses 28,30 to a differential pressure sensor 32. A determination of the flow of gas in the mask 12 is made the differential pressure, $P_2-P_1$, resulting in a flow signal $f_d$. The mask pressure, $P_2$, also is passed to a pressure sensor 34 by a tapped line 36 taken from the respective hose 28, to generate a delivery pressure signals $p_m$, output from the pressure sensor 34.

Both the flow signal, $l_d$, and the pressure signal, $p_m$, are passed to a microcontroller 38 where they are sampled for subsequent signal processing, typically at a rate of 50 Hz.

The microcontroller 38 is programmed to process the flow and pressure signals ($f_d$, $P_m$) to produce an output control signal, $y_o$, provided to an electronic motor servo-controller 42 that, in turn, produces a motor speed control output signal, $V_o$. This signal is provided to the motor 16 to control the rotational speed of the turbine 14 and provide the desired treatment pressure, $P_2$, at the nose mask 12.

The motor servo-controller 42 employs a negative feedback control technique that compares the actual delivery pressure, in the form of the signal $p_m$, with the control signal $y_o$. For convenience, this control stratagem may be independent of operation of the microcontroller 38.

Operation of the controlling of the microcontroller 38, so far as a calculation of respiratory airflow is concerned, broadly is as follows. In a sampled manner, the conductance of any mask leak is calculated, then the instantaneous flow through the leak is calculated. The flow through the leak is subtracted from the total mask flow to calculate the true instantaneous respiratory airflow.

Figure 1A:
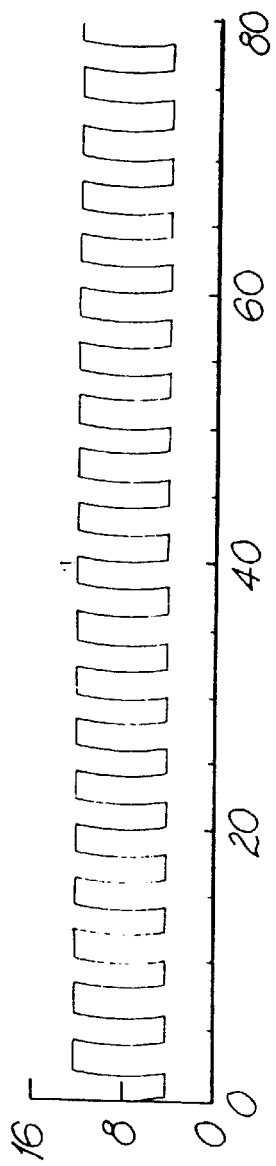
FIGS. 1a–1f shows traces of pressure and airflow from which respiratory airflow is calculated in accordance with a prior art method.
Figure 1B:
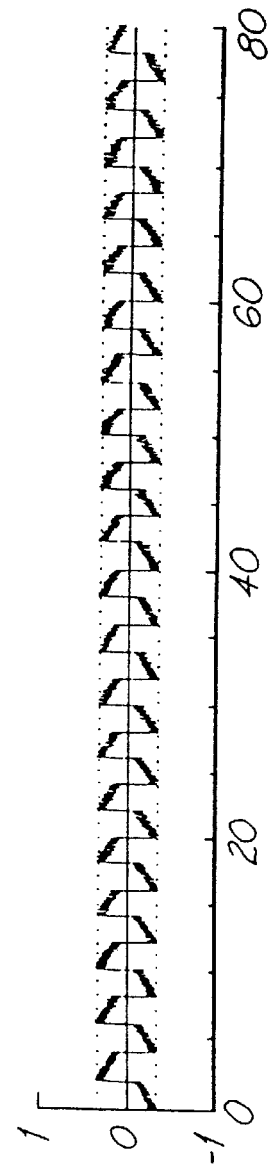
Figure 1C:
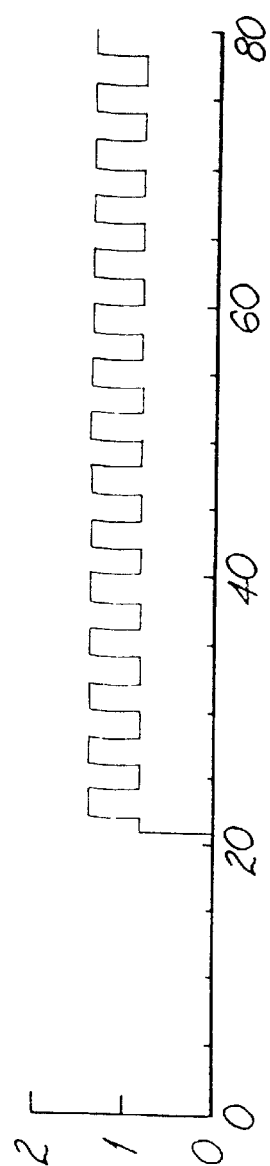
Figure 1D:
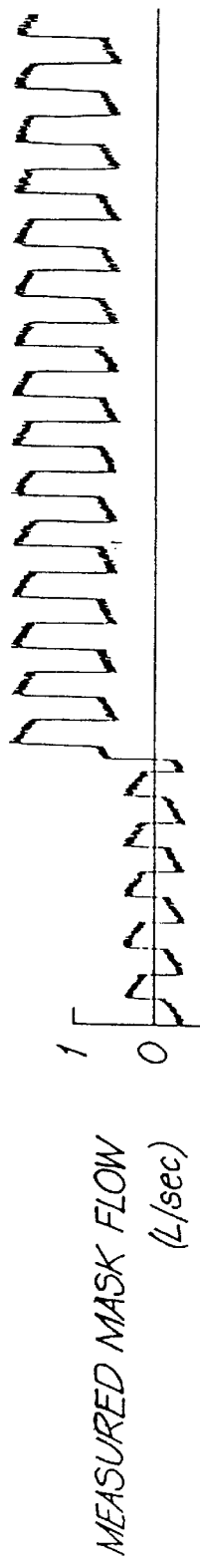
Figure 1E:
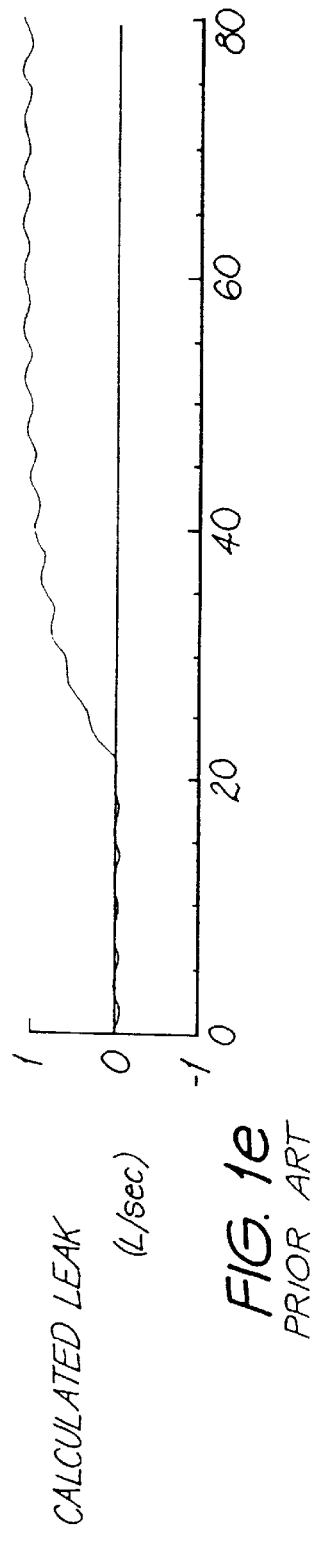
Figure 1F:
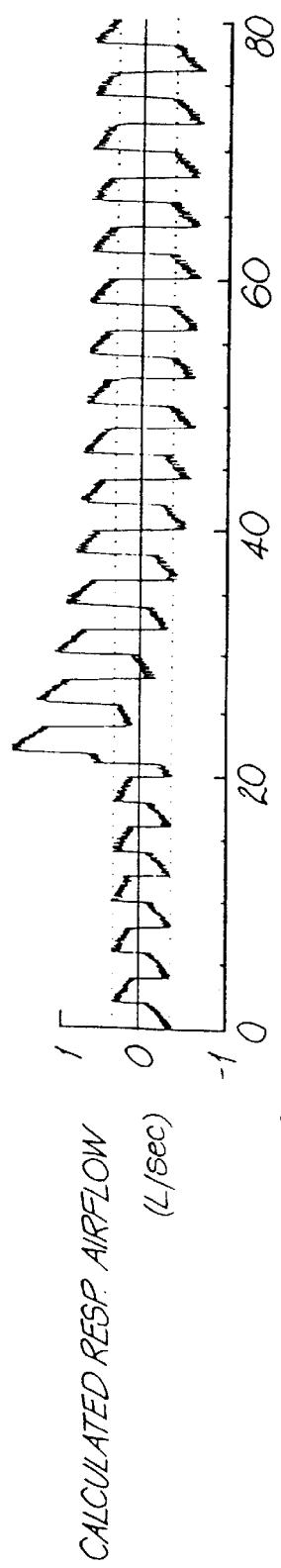
Figure 2B:
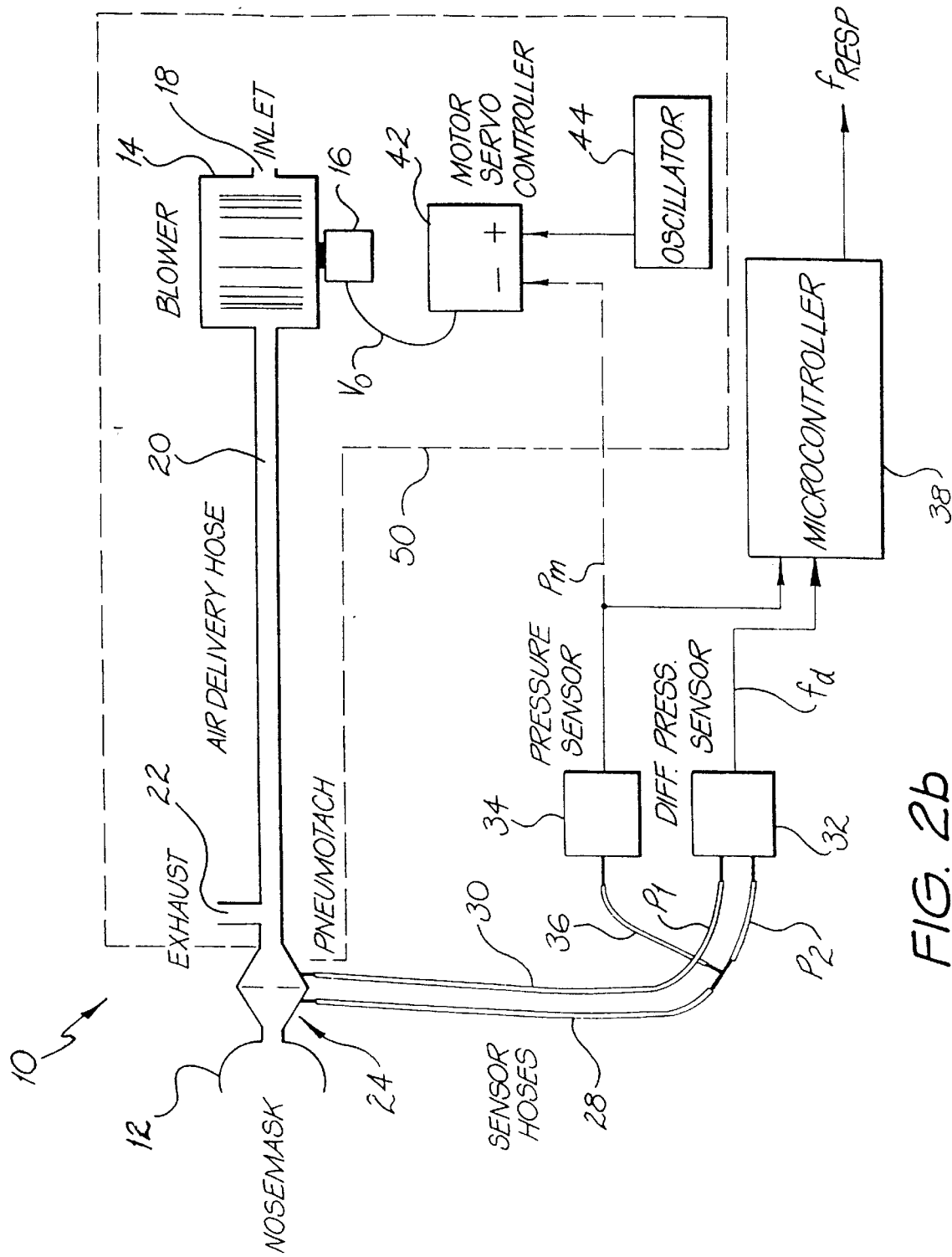

FIG. 2b shows an alternative embodiment of a system for determining true respiratory airflow during mechanical ventilation. The mechanical ventilation system 10' of FIG. 1b differs from that of FIG. 1a firstly in that the microcontroller 38 plays no part in control of the ventilator 50, rather only receives and data processes the electrically transduced mask pressure and flow signals $p_m$, $f_d$ to determine and generate the instantaneous respiratory flow $f_{RESP}$. The ventilator so has an internal drive signal provided by an oscillator 44. The motor servo controller also may or may not receive the mask pressure signal $p_m$ as a form of feedback control. Indeed, the ventilator 50 can be realized by any convenient form of known generic ventilation device.

Figure 3:
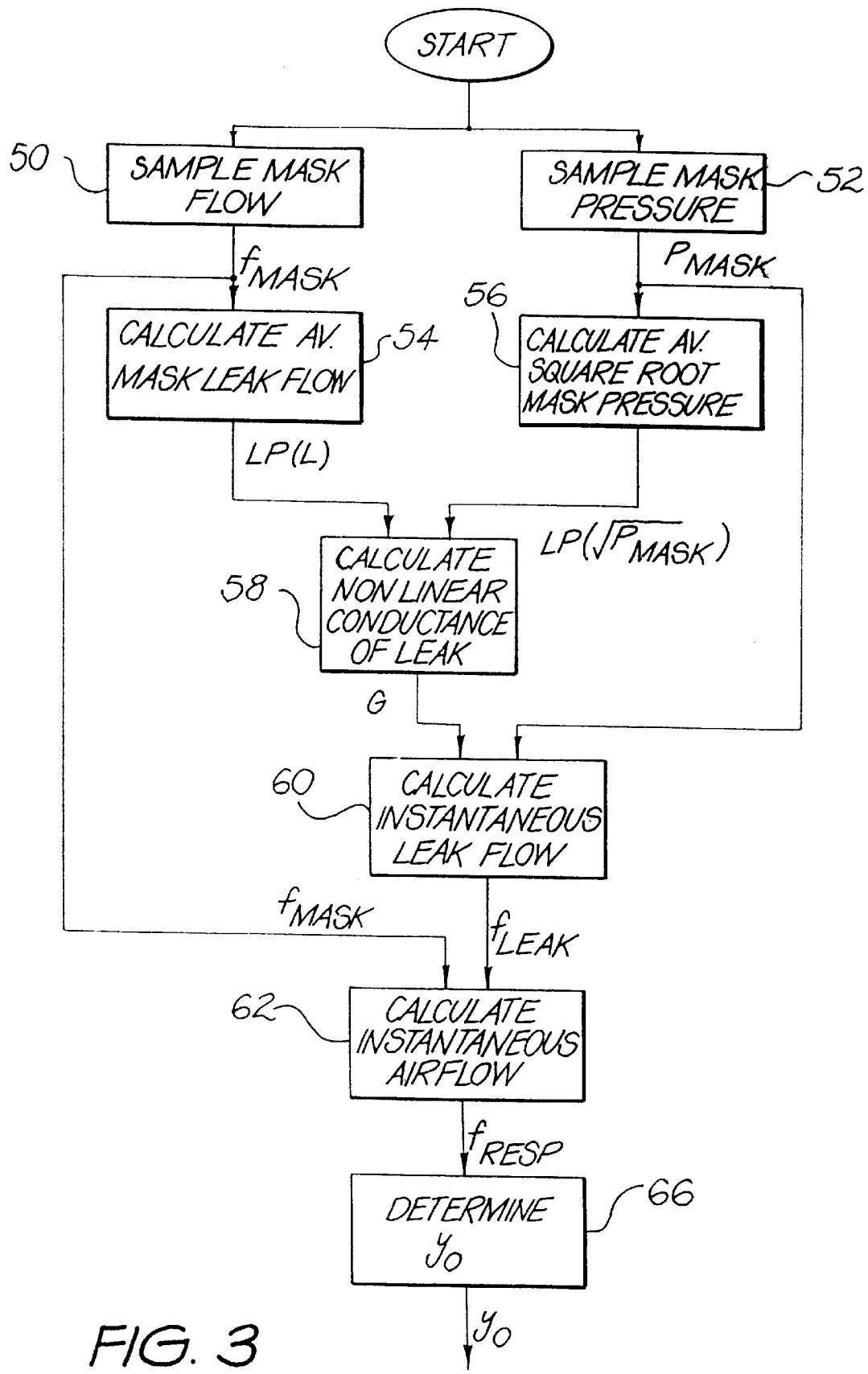
FIG. 3 is a block flow diagram of a method for determining instantaneous respiratory airflow.

The controlling software resident within the microcontroller 38 performs the following steps in determining the respiratory airflow as broadly described above, as also shown in the flow diagram of FIG. 3.

The word "average" is used herein in the most general sense of the result of a low pass filtering step, and is not confined to an arithmetic mean.

1. Repeatedly sample the mask airflow $f_d$ to give a sampled signal $f_{MASK}$, and the mask pressure $P_m$ to give a sampled signal $P_{MASK}$, for example at intervals of T=20 milliseconds. (Steps 50,52).
2. Calculate the average leak, LP(L), as being the result of low pass filtering the airflow, $f_{MASK}$, with a time constant of 10 seconds. (Step 54).
3. Calculate the average of the square root of the mask pressure, $LP(\sqrt{P}_{MASK})$, as being the result of low pass filtering the square root of the mask pressure, $P_{MASK}$, with a time constant of 10 seconds. (Step 56).
4. Calculate the conductance, G, of any leak (step 58), from the equation:

$$G = LP(L)/LP(\sqrt{P}_{MASK})$$

5. Calculate the instantaneous leak flow, $f_{LEAK}$, through the leak (Step 60), from the equation:

$$f_{LEAK} = G\sqrt{P_{MASK}}$$

If there is no leak flow, the value of LP(L) will be equal to zero, as will G and hence $f_{LEAK}$. Thus the methodology is valid also where leak is equal to zero—no leak.

At this juncture the leak flow has been determined, such as would be desired for a leak flow detector. If desired, the instantaneous respiratory airflow can be subsequently determined by the following step.

6. Calculate the instantaneous respiratory airflow, $f_{RESP}$, by subtracting the instantaneous leak from the mask flow (Step 62):

$$f_{RESP} = f_{MASK} - f_{LEAK}$$

FIGS. 4a–4h illustrate the methodology of the embodiment described above with reference to FIG. 2b. At time, t=21 sec, a continuing leak of approximately 1 l/sec is introduced. FIG. 4e shows the mean mask flow. FIG. 4f represents the calculated conductance G, from which the mask leak flow can be estimated as shown in FIG. 4g. Finally, FIG. 4h shows how the calculated respiratory airflow recovers within approximately 30 seconds, and, importantly, gives the correctly scaled (true) magnitude of airflow.

With regard to setting the instantaneous output signal $y_o$, the microcontroller broadly executes the following steps:

7. If the calculated true respiratory airflow $f_{RESP}$ is above a threshold, for example 0.05 L/sec $y_o$ is set to a value corresponding to an inspiratory pressure, $P_{INSP}$. Otherwise $y_o$ is set to a value corresponding to an expiratory pressure $P_{EXP}$. In general, $P_{INSP}$ is higher than $P_{EXP}$, but in the case of continuous positive airways pressure, $P_{EXP}$ may be equal to $P_{INSP}$. (Step 66).

It is to be understood that many other methods of determining $y_o$ from $f_{MASK}$ may be used in step 7, for example as described in the text *Principles and Practice of Mechanical Ventilation*, edited by Martin J. Tobin (McGraw Hill Inc, 1994).

In order to control ventilation, it is necessary to measure the subject's ventilation. In the presence of a leak, the ventilation delivered by the assisted ventilation apparatus is greater than the ventilation delivered to the subject. Known devices which servo-control ventilation cope with this by collecting the exhaled air stream with a complex system of valves, and then measuring the exhaled ventilation. This is inappropriate for devices for use in a domestic setting during sleep, because of the attendant weight, complexity, and expense. The embodiment described compensates for the leak by continuously measuring the nonlinear conductance of the leak, and allowing for the instantaneous flow through the leak as a function of pressure.

Figure 5:
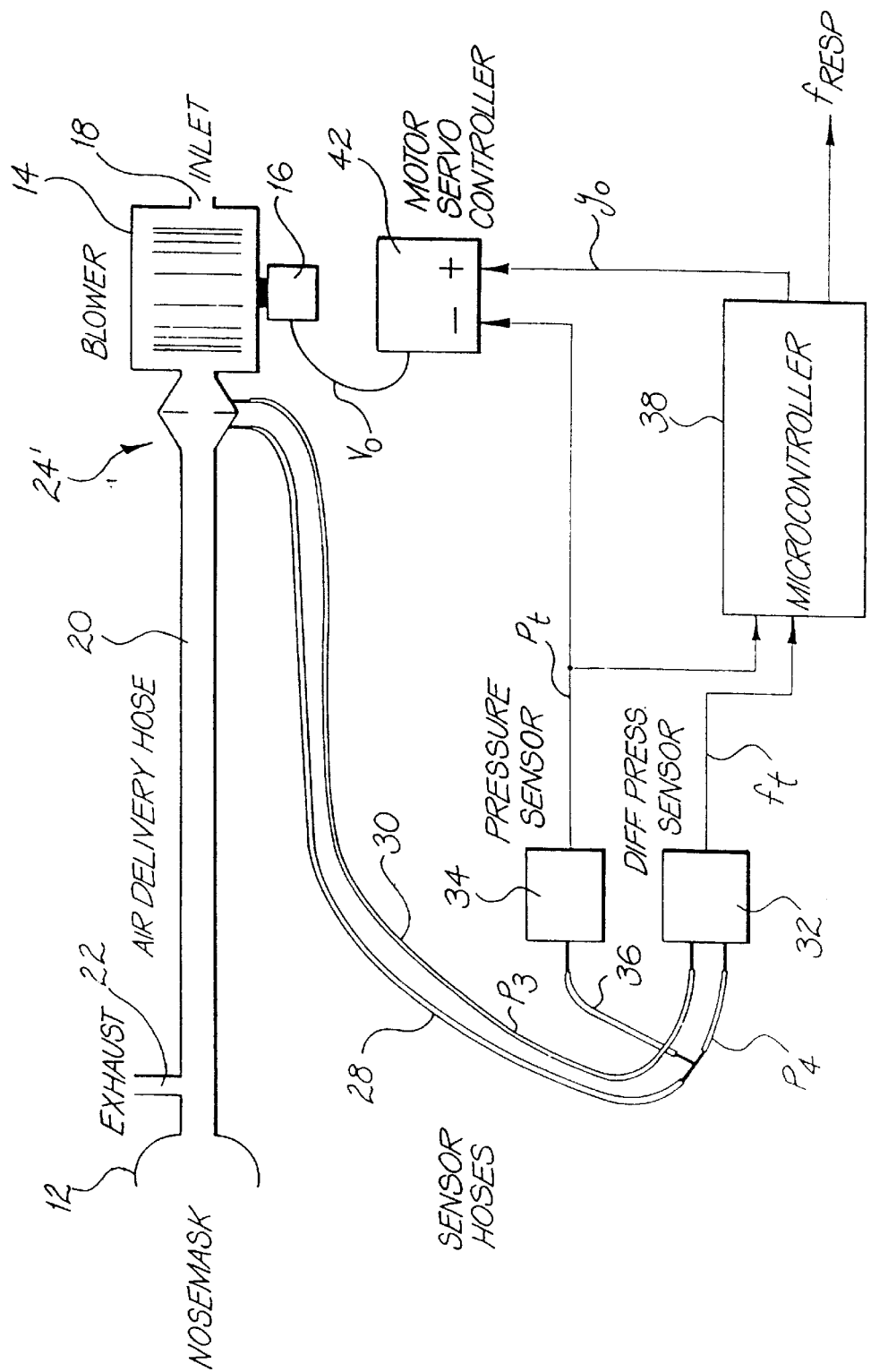
FIG. 5 shows a schematic diagram of ventilatory assistance apparatus of another embodiment.

FIG. 5 shows an alternate arrangement for ventilatory assistance apparatus 10' embodying the invention. In this arrangement, the pneumotachograph 24' is interposed between the turbine 14 and the delivery hose 20.

This arrangement removes the pressure sensing hoses and pneumotachograph from the region of the mask 12. The pressure at the mask, $P_{MASK}$, is calculated from the delivery pressure at the turbine 14, and from the pressure drop down the air delivery hose 20, which for any particular delivery hose is a known function of the flow at the pneumotachograph 24. Further, the microcontroller 38 must also calculate the flow through the mask from the flow at the turbine 14 less the flow through the exhaust 22, which for any particular exhaust is a known function of the pressure at the mask 12.

In more detail, this involves the steps of, firstly measuring the pressure $p_3$ at the turbine 14 with the pressure sensor 34 to produce an electrical signal $p_t$. Next the differential pressure $p_4-p_3$ is measured across the pneumotachograph 24' by the differential pressure sensor 32 to produce an electrical signal $f_t$. In a sampled manner, $p_t$ and $f_t$ are digitized to yield the sampled turbine pressure and flow signals $P_{TURBINE}$ and $F_{TURBINE}$.

The pressure at the mask $P_{MASK}$ and the sampled airflow at the mask $f_{MASK}$ 12 are calculated from the turbine pressure $P_{TURBINE}$ and the flow at the outlet of the turbine $F_{TURBINE}$ as follows:

1. Calculate the pressure drop $\Delta P_{TUBE}$ down the air delivery tube 20, from the flow at the outlet of the turbine $F_{TURBINE}$:

$$\Delta P_{TUBE} = \text{sign}(F_{TURBINE}) \times K_1(F_{TURBINE})^2 + K_2 F_{TURBINE}$$

where $K_1$ and $K_2$ are empirically determined constants, and sign (x) is 1 for $x \geq 0$ and -1 otherwise.

2. Calculate the pressure at the mask, $P_{MASK}$, as the pressure at the turbine $P_{TURBINE}$ less the pressure drop $\Delta P_{TUBE}$ down the air delivery tube 20;

$$P_{MASK} = P_{TURBINE} - \Delta P_{TUBE}$$

3. Calculate the flow, $f_{EXHAUST}$, through the exhaust 22, from the pressure at the mask $P_{MASK}$:

$$f_{EXHAUST} = \text{sign}(P_{MASK}) \times K_3 \sqrt{\text{abs}(P_{MASK})}$$

where $K_3$ is determined empirically.

4. Calculate the flow, $f_{MASK}$, into the mask 12 as the flow at the turbine 14 less the flow through the exhaust 22:

$$f_{MASK} = f_{TURBINE} - f_{EXHAUST}$$

The foregoing embodiments describe low-pass filtering of both the instantaneous airflow and the square root of the instantaneous pressure with a time constant τ of 10 seconds. This time constant, τ, can be advantageously dynamically adjustable.

If the conductance of the leak suddenly changes, then the calculated conductance will initially be incorrect, and will gradually approach the correct value at a rate which will be slow if the time constant of the low pass filters is long, and fast if the time constant is short. Conversely, if the impedance of the leak is steady, the longer the time constant the more accurate the calculation of the instantaneous leak.

Therefore, it is desirable to lengthen the time constant if it is certain that the leak is steady, reduce the time constant if it is certain that the leak has suddenly changed, and to use intermediately longer or shorter time constants if it is intermediately certain that the leak is steady.

If there is a large and sudden increase in the conductance of the leak, then the calculated respiratory airflow will be incorrect. In particular during apparent inspiration, the calculated respiratory airflow will be large positive for a time that is large compared with the expected duration of a normal inspiration. Conversely, if there is a sudden decrease in conductance of the leak, then during apparent expiration the calculated respiratory airflow will be large negative for a time that is large compared with the duration of normal expiration.

Therefore, an index of the degree of certainty that the leak has suddenly changed is derived, such that the longer the airflow has been away from zero, and by a larger amount, the larger the index; and the time constant for the low pass filters is adjusted to vary inversely with the index. In operation, if there is a sudden and large change in the leak, the index will be large, and the time constant for the calculation of the conductance of the leak will be small, allowing rapid convergence on the new value of the leakage conductance. Conversely, if the leak is steady for a long time, the index will be small, and the time constant for calculation of the leakage conductance will be large, enabling accurate calculation of the instantaneous respiratory airflow. In the spectrum of intermediate situations, where the calculated instantaneous respiratory airflow is larger and for longer periods, the index will be progressively larger, and the time constant for the calculation of the leak will progressively reduce. For example, at a moment in time where it is uncertain whether the leak is in fact constant, and the subject merely commenced a large sigh, or whether in fact there has been a sudden increase in the leak, the index will be of an intermediate value, and the time constant for calculation of the impedance of the leak will also be of an intermediate value. One advantage is that some corrective action will occur very early.

Another advantage is that there is never a moment where the leak correction algorithm is "out of control" and needs to be restarted, as described for prior art European Patent Publication No. 0 714 670 A2.

Figure 6:
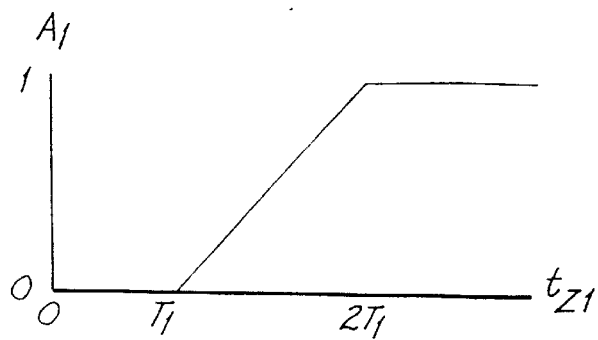
FIG. 6 shows a fuzzy membership function for the calculation of the extent $A_1$ to which the time $t_{Z1}$ since the most recent positive going zero crossing of the calculated respiratory airflow is longer than the expected time $T_1$.
Figure 7:
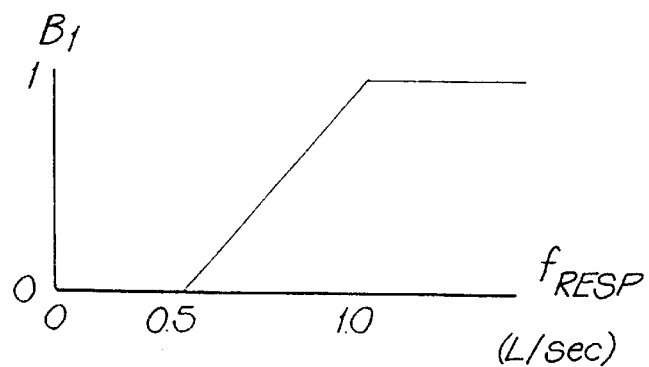
FIG. 7 shows a fuzzy membership function for the calculation of the extent $B_1$ to which the calculated inspiratory respiratory airflow $f_{RESP}$ is large positive.

In a preferred embodiment, the above index is derived using fuzzy logic. The fuzzy extent $A_1$ to which the airflow has been positive for longer than expected is calculated from the time $t_{Z_I}$ since the last positive-going zero crossing or the calculated respiratory airflow signal, and the expected duration $T_1$ of a normal inspiration for the particular subject, using the fuzzy membership function shown in FIG. 6. The fuzzy extent $B_I$ to which the airflow is large and positive is calculated from the instantaneous respiratory airflow using the fuzzy membership function shown in FIG. 7. The instantaneous index $I_I$ of the degree of certainty that the leak has suddenly increased is calculated as the fuzzy intersection (lesser) of $A_1$ and $B_I$.

Figure 8:
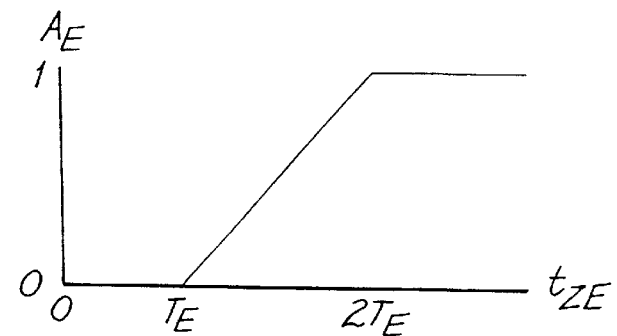
FIG. 8 shows a fuzzy membership function for the calculation of the extent $A_E$ to which the time $t_{ZE}$ since the most recent negative going zero crossing in the calculated respiratory airflow is longer than the expected time $T_E$.
Figure 9:
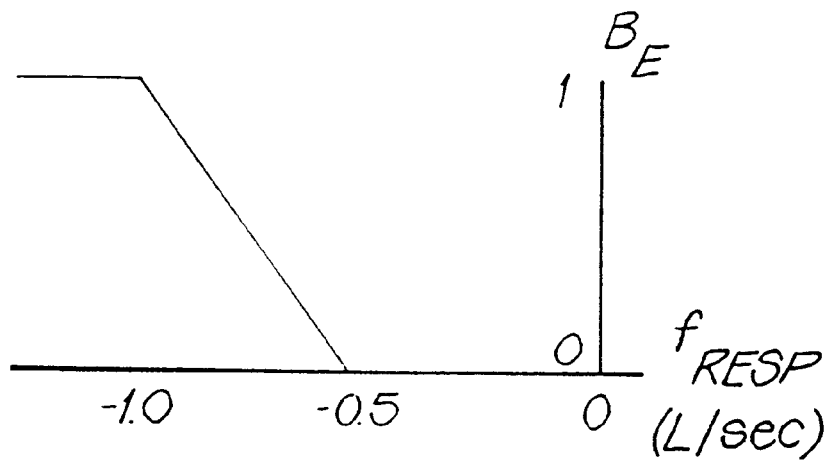
FIG. 9 shows a fuzzy membership function for the calculation of the extent $B_E$ to which the respiratory airflow $f_{RESP}$ is large negative.

Comparable calculations are performed for expiration as follows. The fuzzy extent $A_E$ to which the airflow has been negative for longer than expected is calculated from the time $t_{ZE}$ since the last negative-going zero crossing of the calculated respiratory airflow signal, and $T_E$, the expected duration of a typical expiration for the particular subject, using the membership function shown in FIG. 8. The fuzzy extent $B_E$ to which the airflow is large negative is calculated from the instantaneous respiratory airflow using the fuzzy membership function shown in FIG. 9. The instantaneous index $I_E$ of the degree of certainty that tie leak has suddenly decreased is calculated as the fuzzy intersection of $A_E$ and $B_E$.

Figure 10:
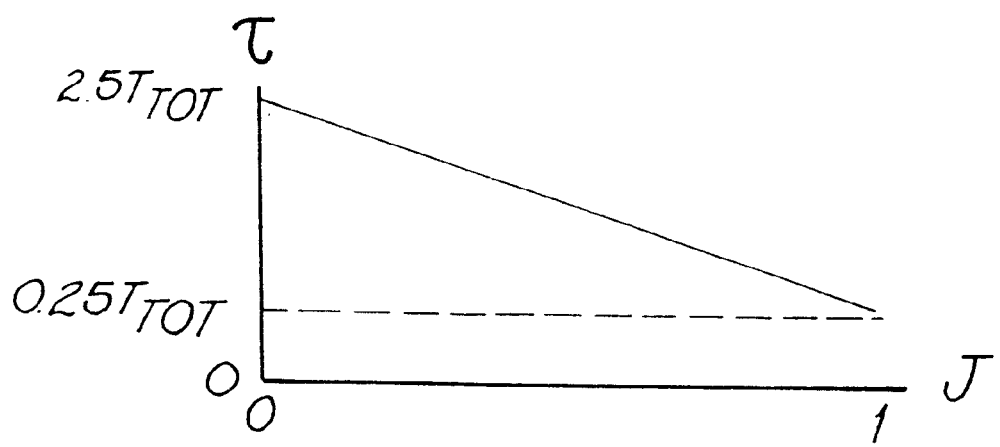
FIG. 10 shows the relation between an index J and time constant τ.

The instantaneous index I of the extent to which there has been a sudden change in the leak (either an increase or a decrease) is calculated as the fuzzy union (larger) of indices $I_I$ and $I_E$. The instantaneous index I is then passed through a peak detector followed by a low pass filter with a time constant of, for example 2 seconds, to yield the desired index J. Thus if index I becomes momentarily large, index J will be initially large and remain so for a few seconds. The time constant $\tau$ for the low pass filters used in the calculation of the conductance of the leak is then adjusted to vary inversely with the index J, as shown in FIG. 10. For example, if the expected duration of a normal respiratory cycle were 4 seconds the time constant is set to 10 seconds if the index J is zero, (corresponding to complete certainty that the leak is steady), and to 1 second if the index J is unity (corresponding to complete certainty that the leak is suddenly changing), and to intermediate values for intermediate cases.

The embodiments described refer to apparatus for the provision of ventilatory assistance, however, it is to be understood that the invention is applicable to all forms of mechanical ventilation and apparatus for the provision of continuous positive airway pressure treatment. The apparatus can be for die provision of a constant treatment pressure, multi-level (IPAP and EPAP) treatment or autosetting (adjusting) treatment or other forms of mechanical ventilation, including Proportional Assist Ventilation (PAV) as taught by M Younes in the above-noted text.

The methodology described can be implemented in the form of a computer program that is executed by the microcontroller described, or by discrete combinational logic elements, or by analog hardware.

I claim:

1. A method for determining instantaneous leak flow at a mask having a leak path during mechanical ventilation, the method comprising the steps of:

(a) determining instantaneous airflow at the mask;

(b) determining instantaneous pressure at the mask;

(c) estimating non-linear instantaneous conductance of said leak path as the low-pass filtered instantaneous airflow divided by the low-pass filtered square root of the instantaneous pressure; and (d) determining said instantaneous leak flow to be said conductance multiplied by the square root of the said instantaneous pressure.

2. A method for determining instantaneous respiratory airflow for a subject receiving breathable gas by a mask and in the presence of any mask leak, the method comprising the steps of:

(a) determining instantaneous airflow at the mask;

(b) determining instantaneous pressure at the mask;

(c) estimating non-linear instantaneous conductance of said leak path as the low pass filtered instantaneous airflow divided by the low pass filtered square root of the instantaneous pressure;

(d) determining instantaneous leak flow to be said conductance multiplied by the square root of the said instantaneous pressure; and (e) calculating the respiratory airflow as the instantaneous airflow minus the instantaneous leak flow.

3. A method as claimed in claim 2, whereby the time constants for said low pass filtering are dynamically adjustable dependent upon sudden changes in said instantaneous leak flow.

4. A method as claimed in claim 3, whereby said dynamic adjustment comprises the further steps of:

deriving an index of the extent to which said conductance has changed suddenly; and changing said time constants in an opposite sense to a corresponding change in said index.

5. A method as claimed in claim 4, whereby said index is derived by the steps of:

from said calculated respiratory airflow, determining the extent to which the absolute magnitude of calculated airflow is larger than expected for longer than expected.

6. A method as claimed in claim 2, whereby steps (a) and (b) comprise:

measuring airflow and pressure in a gas delivery circuit coupled to said mask;

calculating the pressure drop along the delivery circuit to the mask as a function of said delivery circuit airflow; and calculating a derived said instantaneous mask pressure as tie measured delivery circuit pressure less the pressure drop; and calculating the airflow through an exhaust of the mask as a function of the derived instantaneous mask pressure; and calculating a derived said mask airflow as the measured delivery circuit airflow minus the exhaust airflow.

7. Apparatus for determining respiratory airflow for a subject receiving breathable gas by a mask and in the presence of any mask leak, the apparatus comprising:

transducer means located at or proximate the mask and in fluid communication therewith to provide signals representing instantaneous mask airflow and pressure; and processing means receiving said airflow and pressure signals for estimating non-linear instantaneous conductance of said leak path as the low pass filtered instantaneous airflow divided by the low pass filtered square root of the instantaneous pressure, determining instantaneous leak flow to be said conductance multiplied by the square root of the said instantaneous pressure, and calculating the respiratory airflow as the instantaneous airflow minus the instantaneous leak flow.

8. Apparatus as claimed in claim 7, wherein the time constants for said low pass filtering are dynamically adjustable dependent upon sudden changes in said instantaneous leak flow.

9. Apparatus as claimed in claim 8, wherein said processor means dynamically adjusts the time constants by deriving an index of the extent to which said conductance has changed suddenly, and changing said time constants in an opposite sense to a corresponding change in said index.

10. Apparatus as claimed in claim 9, wherein said processor means derives said index from said calculated respiratory airflow by determining the extent to which the absolute magnitude of calculated airflow is larger than expected for longer than expected.

11. Apparatus as claimed in claim 7, wherein said transducer means comprises a pneumotachograph coupled to a differential pressure transducer.

12. Apparatus as claimed in claim 11, wherein said pneumotachograph is located between the mask and the mask exhaust.

13. Apparatus as claimed in claim 11, wherein said transducer means is located in a gas delivery circuit connected with said mask and remote from said mask.

14. Apparatus for providing continuous positive airway pressure treatment or mechanical ventilation, the apparatus comprising:

a turbine for the generation of a supply of breathable gas;

a gas delivery tube having connection with the turbine;

a mask having connection to the delivery tube to supply said breathable gas to a subject's airway;

transducer means located at or proximate the mask and in fluid communication therewith to provide signals representing instantaneous mask airflow and pressure;

processor means receiving said airflow and pressure signals for estimating non-linear instantaneous conductance of said leak path as the low pass filtered instantaneous airflow divided by the low pass filtered square root of the instantaneous pressure, determining instantaneous leak flow to be said conductance multiplied by the square root of the said instantaneous pressure, and calculating the respiratory airflow as the instantaneous airflow minus the instantaneous leak flow; and control means to control the flow generator to, in turn, control the mask pressure and/or mask airflow on the basis of the calculated respiratory airflow.

15. Apparatus as claimed in claim 14, wherein the time constants for said low pass filtering are dynamically adjustable dependent upon sudden changes in said instantaneous leak flow.

16. Apparatus as claimed in claim 15, wherein said processor means dynamically adjusts the time constants by deriving an index of the extent to which said conductance has changed suddenly, and changes said time constants in an opposite sense to a corresponding change in said index.

17. Apparatus as claimed in claim 16, wherein said processor means derives said index from said calculated respiratory airflow by determining the extent to which the absolute magnitude of calculated airflow is larger than expected for longer than expected.

18. A computer program for determining instantaneous respiratory airflow for a subject receiving breathable gas by a mask and in the presence of any mask leak, the program receiving input data of instantaneous airflow and pressure at the mask, and comprising the computational steps of:

(a) determining instantaneous airflow at the mask;

(b) determining instantaneous pressure at the mask;

(c) estimating non-linear instantaneous conductance of said leak path as the low pass filtered instantaneous airflow divided by the low pass filtered square root of the instantaneous pressure;

(d) determining instantaneous leak flow to be said conductance multiplied by the square root of the said instantaneous pressure; and (e) calculating the respiratory airflow as the instantaneous airflow minus the instantaneous leak flow.

* * * * *

UNITED STATES PATENT AND TRADEMARK OFFICE
CERTIFICATE OF CORRECTION

PATENT NO. : 6,152,129
DATED : November 28, 2000
INVENTOR(S) : Berthon-Jones

It is certified that error appears in the above-identified patent and that said Letters Patent is hereby corrected as shown below:

Column 1,
Line 58, change "ofifset" to -- offset --

Claim 6,
Line 9, change "tie" to -- the --

Signed and Sealed this

Sixteenth Day of October, 2001

Attest:

*Attesting Officer*

NICHOLAS P. GODICI
*Acting Director of the United States Patent and Trademark Office*